(12) United States Patent
Landanger

(10) Patent No.: US 9,775,710 B2
(45) Date of Patent: Oct. 3, 2017

(54) SURGICAL DEVICE

(71) Applicant: LANDANGER, Chaumont (FR)

(72) Inventor: Benoît Landanger, Ruffey les Echirey (FR)

(73) Assignee: LANDANGER, Chaumont (FR)

( * ) Notice: Subject to any disclaimer, the term of this patent is extended or adjusted under 35 U.S.C. 154(b) by 390 days.

(21) Appl. No.: 14/606,398

(22) Filed: Jan. 27, 2015

(65) Prior Publication Data

US 2016/0213471 A1 Jul. 28, 2016

(51) Int. Cl.
*A61F 2/24* (2006.01)

(52) U.S. Cl.
CPC .......... *A61F 2/2466* (2013.01); *A61F 2/2457* (2013.01)

(58) Field of Classification Search
CPC . A61B 17/0469; A61B 17/0487; A61B 17/29; A61B 17/0482; A61B 2017/00243; A61B 2017/00349; A61B 2017/0409; A61F 2/2457; A61F 2/2466; A61F 5/0086
USPC ....... 606/139, 144, 148, 205, 206; 623/2.11, 623/904
See application file for complete search history.

(56) References Cited

U.S. PATENT DOCUMENTS

| 7,635,386 B1 | 12/2009 | Gammie |
| 2005/0251177 A1 | 11/2005 | Saadat et al. |
| 2006/0271101 A1 * | 11/2006 | Saadat ............... A61B 17/0469 606/205 |
| 2007/0049952 A1 | 3/2007 | Weiss |
| 2009/0105751 A1 | 4/2009 | Zentgraf |
| 2010/0113873 A1 | 5/2010 | Suzuki et al. |
| 2013/0317291 A1 | 11/2013 | Yamamoto |

FOREIGN PATENT DOCUMENTS

| WO | 2012-096280 A1 | 7/2012 |
| WO | 2013-008817 A1 | 2/2015 |

OTHER PUBLICATIONS

European Search Report dated Oct. 8, 2014, in connection with EP Application No. 14 17 8466 (2 pgs.).

* cited by examiner

*Primary Examiner* — Katherine M Shi
(74) *Attorney, Agent, or Firm* — Maier & Maier, PLLC

(57) ABSTRACT

Surgical device including a hollow cylinder, a clamp having of two jaws, including an outer surface and an inner surface, pivotably mounted relative to an axis perpendicular to the longitudinal axis of said hollow cylinder between an open position and a closed position, wherein the clamp is arranged extending from the distal end of said hollow cylinder and two hollow tubes, partially housed inside said hollow cylinder, wherein said jaws each have a passage from said outer surface to said inner surface, said passages being arranged facing each other when said clamp is in the closed position and in that each of said hollow tubes is associated respectively with one of the jaws in such a way that said hollow tube opens into said passage.

10 Claims, 4 Drawing Sheets

Fig. 2

SURGICAL DEVICE

FIELD OF THE INVENTION

The present invention relates particularly to a surgical device which may be particularly used for fitting mitral chordal prostheses. Furthermore, the present invention also relates to a method for fitting mitral chordal prostheses using the device according to the invention.

The mitral valve is a valve separating the left atrium from the left ventricle. It more particularly consists of a fibrous band, having two leaflets, joined to the left ventricular muscle by muscle pillars, via fibrous chordae.

Opening and closing of the mitral valve is triggered by the pressure differential between the left atrium and the left ventricle. During the ventricular dilatation phase, the valve is opened enabling blood flow from the atrium to the ventricle. At the start of ventricular contraction, the pressure therein rises suddenly, the valve is closed and prevents backflow.

Mitral insufficiency is a common condition of the heart valves caused by poor closure of the two leaflets thereof, inducing blood backflow in the left atrium during the blood expulsion phase. Severe forms of mitral insufficiency may require a surgical procedure.

The main causes of mitral insufficiency are coronary disease, cardiomyopathy, or mitral prolapse. It may also occur in the case of other congenital heart defects.

The treatment depends on the extent of the leakage, the repercussions thereof on the left ventricle and predisposition.

Surgical treatment may consist either of valve reconstruction (mitral plasty), or replacement of the mitral valve by a prosthesis (artificial valve): mechanical valve or bioprosthetic valve.

In the context of mitral plasty, the surgeon inspects the mitral valve damage thoroughly. According to the nature of the mitral valve damage, the surgeon performs valve suture or valve chordal repair. A band is very often placed around the valve to ensure that the valve leaflets are tight. In some cases, if the valve is perforated, the surgeon makes a patch (small membrane) using a piece of pericardium (tissue surrounding the heart) removed from the patient during the procedure.

In the context of this procedure, it may thus be necessary to replace the mitral chordae by a prosthesis in the form of a Goretex thread.

There is thus a need for a device suitable for introducing the prosthesis into the heart and inserting same on the mitral valve.

SUMMARY OF THE INVENTION

The present invention relates particularly to a surgical device comprising a hollow cylinder, a clamp consisting of two jaws, comprising an outer surface and an inner surface, pivotably mounted relative to an axis perpendicular to the longitudinal axis of said hollow cylinder between an open position and a closed position, wherein the clamp is arranged extending from the distal end of said hollow cylinder and two hollow tubes, characterized in that said jaws each comprise a passage from said outer surface to said inner surface, said passages being arranged facing each other when said clamp is in the closed position and in that each of said hollow tubes is associated respectively with one of the jaws in such a way that said hollow tube opens into said passage.

According to one preferred embodiment of the invention, said hollow tubes are flexible.

According to one preferred embodiment of the invention, said hollow tubes are housed partially inside said hollow cylinder.

According to one preferred embodiment of the invention, the distal end of said hollow tubes is rotatably mounted, about an axis perpendicular to the longitudinal axis of said passage, between a high position wherein the distal end of said hollow tube extends from said passage and a low position wherein the distal end of said hollow tube is arranged perpendicularly to said passage.

According to one more preferred embodiment of the invention, the outer surface of said jaws comprises at the outer surface thereof a groove intended to receive the distal part of said hollow tube when said tube is in the low position.

According to one preferred embodiment of the invention, the rotation of said jaws is actuated by a rod, positioned wholly or partially in said hollow cylinder, wherein the proximal end opens at the proximal end of said hollow cylinder and wherein the distal end is associated with the proximal end of said jaws.

According to one preferred embodiment of the invention, the inner surface of said jaws comprises ribs.

According to one more preferred embodiment of the invention, said ribs have a triangular transverse profile.

According to one preferred embodiment of the invention, said hollow cylinder comprises at the distal end thereof an opening arranged extending from said groove and intended to enable the passage of said hollow tube from inside to outside said cylinder.

According to one preferred embodiment of the invention, said hollow cylinder comprises in the proximal part thereof openings intended to enable the passage of said hollow tubes from inside to outside said hollow cylinder.

According to one preferred embodiment of the invention, the distal end of said clamp has a curved longitudinal profile.

According to one preferred embodiment of the invention, the end of said clamp has a semicircular longitudinal profile in the closed position.

According to one preferred embodiment of the invention, said clamp is associated with said hollow cylinder via an intermediate part comprising a proximal part, inserted into the distal end of said hollow cylinder, and a distal part comprising recesses suitable for receiving the axis guiding said jaws in rotation.

BRIEF DESCRIPTION OF THE FIGURES

FIG. 2 shows a longitudinal sectional view of the embodiment of the invention shown in FIG. 1.

DESCRIPTION OF EMBODIMENTS

Figure 1:
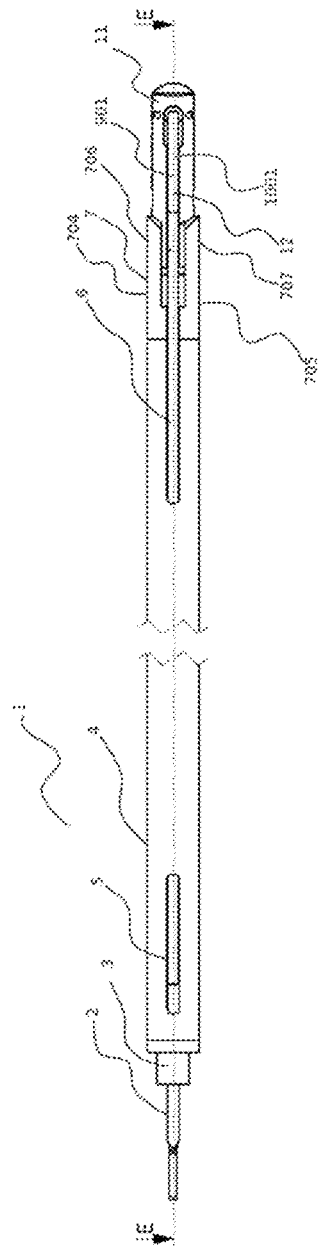
FIG. 1 shows a top view of one embodiment of a device according to the invention.
Figure 2:
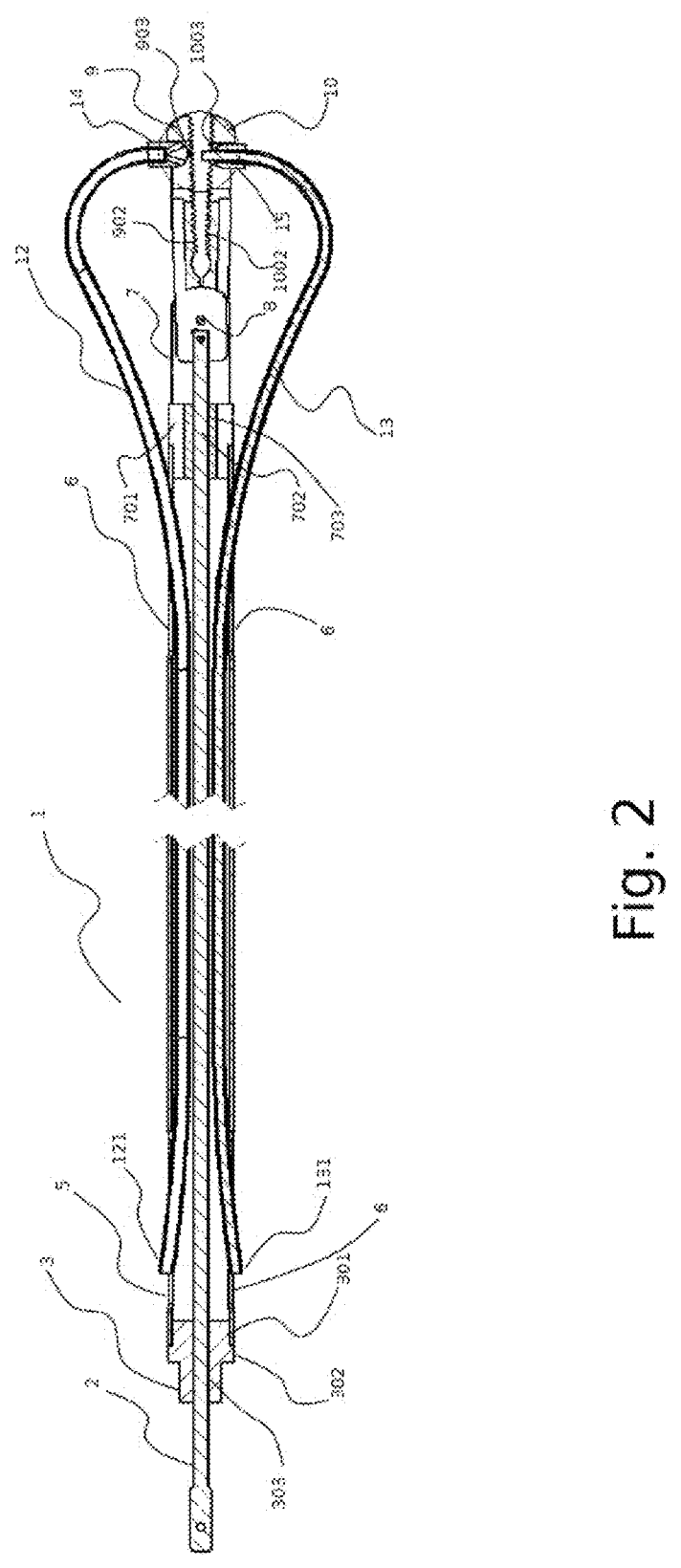

With reference to FIGS. 1 and 2, the device 1 according to the invention comprises from the proximal end thereof to the distal end thereof: the free end of the rod 2, the sealing plug 3, the hollow cylinder 4 comprising, on the top face thereof and on the bottom face thereof, an opening in the form of an oblong hole 5 and a groove 6 in the axis of the oblong hole, the intermediate part 7 supporting the axis 8 about which the jaws 9, 10 are rotated.

The groove 6 extends to the distal end of said hollow cylinder followed by at the level of the intermediate part 7 followed by along the outer surface of the adjacent jaw 9. This groove 6 is intended to receive a hollow tube 12, 13 when said tube is in the low position. As such, it is understood that when the clamp 11 is closed, and the hollow tubes 12, 13 in the low position, the whole device 1 according to the invention fits completely into a cylinder having a diameter equal to that of said hollow cylinder.

With reference to FIG. 2, the sealing plug 3 preferentially comprises a throat 301 inserted inside the cylinder and a shoulder 302 bearing on the proximal end of the cylinder. This sealing plug 3 comprises a bore 303 for inserting the rod 2. The sealing plug 3 is preferentially made of a material suitable for ensuring tightness at the bore/rod 2 junction. It is thus suitable for sealing the hollow cylinder 4 and holding the rod 2 along an axis parallel with the longitudinal axis of the hollow cylinder 4.

The hollow cylinder 4 has a diameter preferentially between 3 and 10 millimeters. The distal end thereof is closed by the intermediate part 7, the proximal part whereof forms a plug 701 inserted inside the hollow cylinder 4. The external part of this plug 701 has an equivalent diameter to the diameter of the hollow cylinder 4. This plug is bored to enable insertion of the rod 2, this rod 2 is thus supported both by the sealing plug 3 at the proximal part of the hollow cylinder 4 and by the intermediate part 7 situated at the distal part of said hollow cylinder 4. The bore 702 of said intermediate part 7 is preferentially covered with a cylindrical seal 703.

The intermediate part 7 further comprises a second part consisting of two strips 704, 705 extending towards the clamp 11 and supporting the axis 8 intended to hold the jaws 9, 10. The axis 8 is held, at the ends thereof, in a perforated hole 706, 707 in each of said strips 704, 705. The gap between the two strips is situated extending from the groove 6, present on the first part of the intermediate part 7.

The clamp 11 thus consists of two jaws 9, 10 held in rotation about the axis 8 between an open position and a closed position. The change from the open position to said closed position is preferentially made by means of the rod 2, the distal end whereof is associated with the jaws 9, 10 of the clamp 11 by means of a connecting rod/groove type arrangement.

The outer surface of said jaws 9,10 comprises a groove 901, 1001 positioned extending from the gap between the two strips 704, 705 of the intermediate part 7. The inner surface of said jaws 9, 10 comprises ribs 902, 1002 for enhancing the hold of the clamp 11 at the valve when said clamp 11 is in the closed position. Said ribs 902, 1002 preferentially have a triangular transverse profile. However, it is understood that said profile may be modified according to requirements.

In order to facilitate the penetration of the device 1 according to the invention inside the body of the patient to be treated, the distal end of the clamp 11 preferentially has a curved surface and more preferentially a hemispherical surface.

Each of the two jaws 9, 10 comprises an inner surface and an outer surface and a passage 903, 1003 from the outer surface thereof to the inner surface thereof arranged such that said passages 903, 1003 are facing when the clamp 11 is in the closed position.

The device 1 according to the invention further comprises two hollow tubes 12, 13 open at each of the ends thereof. Each of said hollow tubes 12, 13 is partially housed inside the hollow cylinder 4 and comprises a free end 121,131, opening outside the hollow cylinder 4 via the oblong hole 5 placed at the proximal part of the hollow cylinder 4, and one end associated with a jaw 9, 10 of the clamp 11. In order to ensure the tightness of the hollow cylinder 4, said oblong hole 5 and/or said groove 6 are sealed by a seal enabling the insertion of said hollow tube 12, 13.

The arrangement between the end of the hollow tube 12, 13 and the jaw 9, 10 is carried out such that the opening of the tube 12, 13 at this end is flush with the passage 903, 1003 of said jaw, when said hollow tube 9, 10 is in the high position, such that said hollow tube 9, 10 opens into said passage 903, 1003.

Advantageously, the distal end of the hollow tubes 12, 13 is rotatably mounted, about an axis perpendicular to the longitudinal axis of said passage 903, 1003, between a high position wherein the distal end of said hollow tube 12, 13 extends from said passage 903, 1003 and a low position wherein the distal end of said hollow tube 12, 13 is arranged perpendicularly to said passage 903, 1003. Preferentially, this arrangement is made via a cylindrical head 14, 15 comprising a bore wherein the distal end of said hollow tube 12, 13 is inserted. This cylindrical head comprises two pins 16, 17, arranged coaxially on either side of the outer surface thereof, inserted into two congruent housings 18, 19 arranged inside said passage 903, 1003. It is thus understood that the cylindrical head 14, 15 will be able to pivot, about the axis defined by the pins 16, 17, between a high position and a low position.

The arrangement between the distal end of the hollow tube 12, 13 and the bore of the cylindrical head 14, 15 is preferentially made by bonding. Preferentially, one of the two cylindrical heads, or transmitting head 15, is associated at the distal end of the hollow tube 13 along the entire length of the bore thereof. The distal end of the hollow tube 13 is thus flush at the distal end of the cylindrical head 15. The other cylindrical head, or receiving head 14, comprises, from the proximal end thereof to the distal end thereof a bore extended by a countersink opening out toward the distal end of said receiving head 16. In this case, the distal end of the hollow tube 12 is associated with the bore of said receiving head 16 and is flush with the entrance of the countersink. It is thus understood that the countersink will enable the passage of the mitral chordae from the transmitting head 15 to the receiving head 14. Furthermore, this passage is enhanced further in that the heads 14, 15 are rotatably mounted relative to the rest of the jaw and not locking facing each other. As such, the position of the heads 14, 15 may be adapted optimally during the passage of the chordae.

The distal end of said cylindrical heads 14, 15 preferentially has a hemispherical surface.

In the low position, the distal end of said hollow tube 12, 13 is positioned perpendicularly to the longitudinal axis of the passage 9003, 1003 joining the inner surface to the outer surface of the jaw 9,10. The hollow tube 12, 13 is thus housed entirely inside the groove 901, 1001 present on the outer surface of said jaw followed by in the gap between the two strips of the intermediate part 7 followed by in the groove 6 at the surface of the first part of said intermediate part 7. In this position, said hollow tube 12, 13 is thus entirely housed inside the parts forming the rest of the device 1 according to the invention.

In the high position, the distal end of said hollow tube 12, 13 extends from said passage 903, 1003 joining the outer surface to the inner surface of said jaw 9, 10. Changing from the high position to the low position is carried out by pushing on the free end 121, 131 of said tube 12, 13 which rotates the cylindrical head 14,15 about the pins 16, 17 thereof. Changing from the high position to the low position is carried out by means of a reverse movement.

Figure 3:
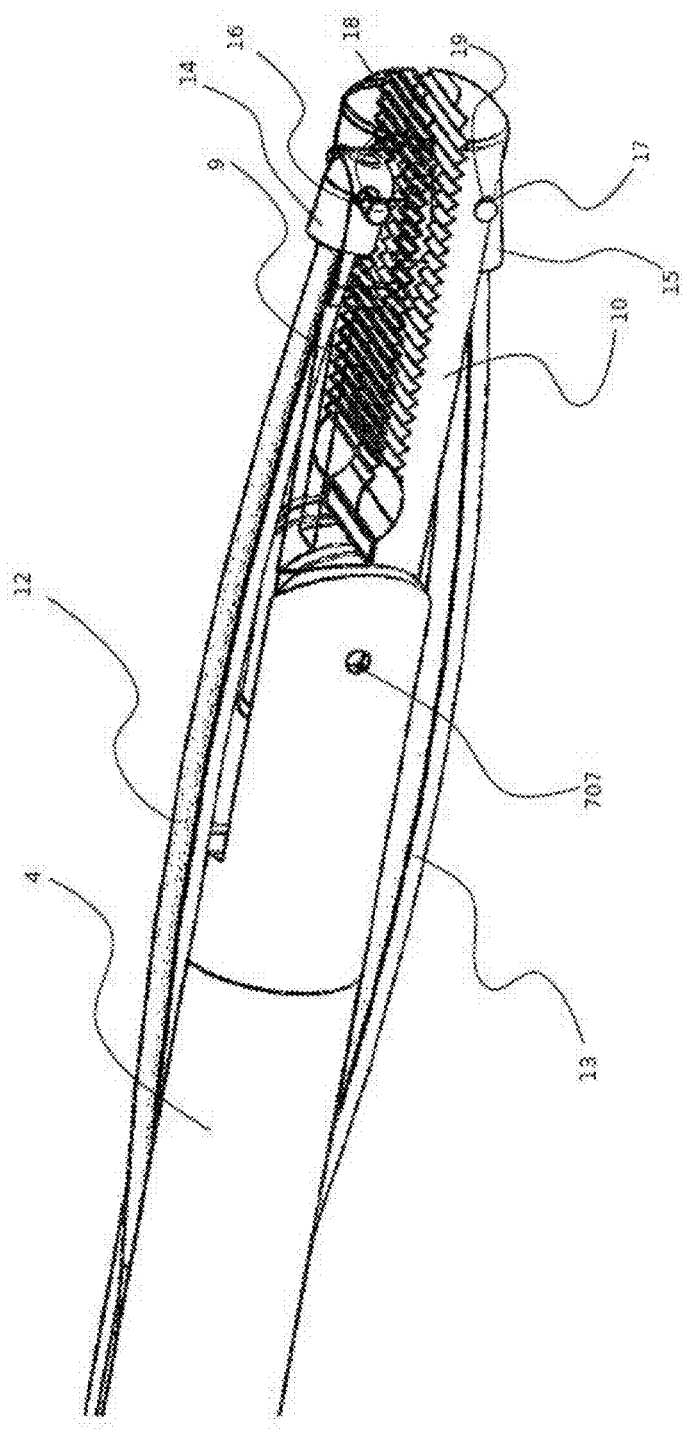
FIG. 3 shows a perspective view of a device according to the invention with the clamps in the open position.
Figure 4:
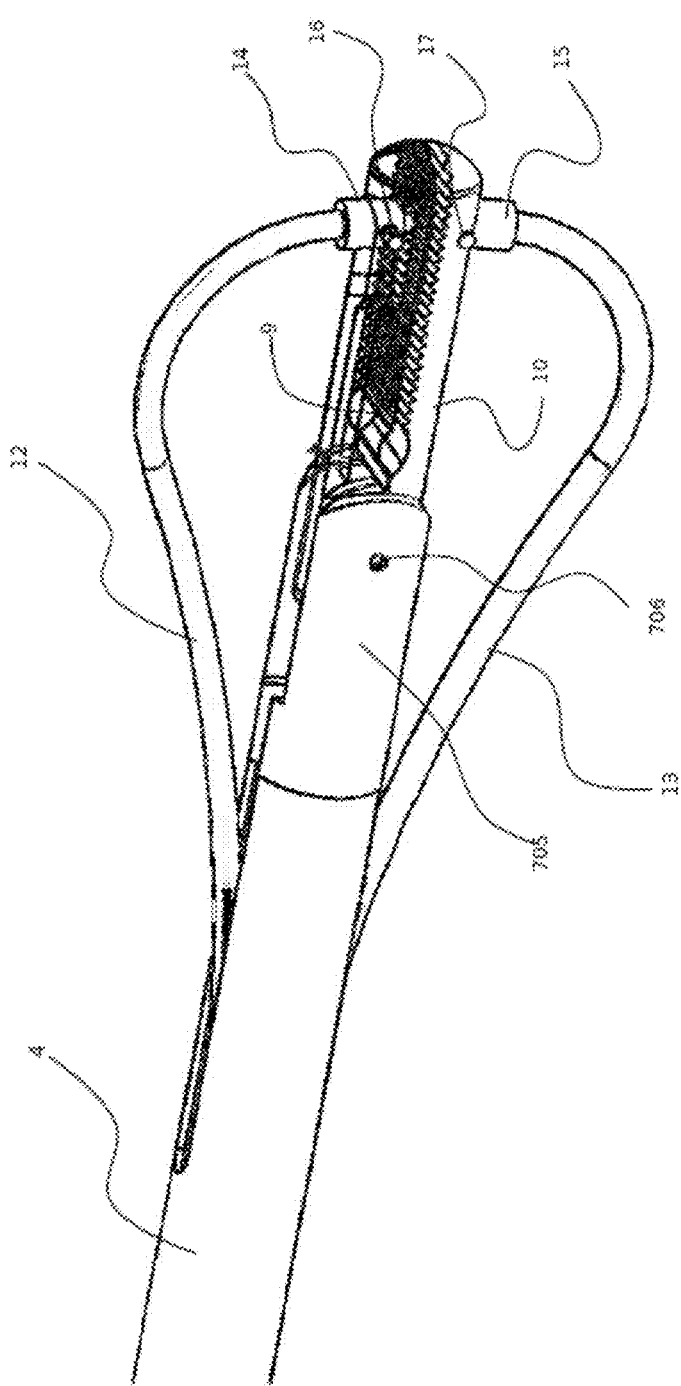
FIG. 4 shows a perspective view of a device according to the invention with the clamps in the closed position.

The device 1 according to the invention functions as follows:

1. The practitioner inserts the clamp 11 into the patient's heart with the hollow tubes 12, 13 in the low position (see FIG. 3).
2. He/she opens the jaws 9,10 in order to grip the mitral valve.
3. He/she locks the clamp 11 in the closed position on the mitral valve.
4. He/she pushes on the hollow tubes 12, 13 to set the tubes in the high position.
5. He/she then inserts a flexible thin rod to which the Goretex chordal prosthesis is attached in the elements in the following order:
    a. The hollow tube 13 associated with the cylindrical transmitting head 15
    b. The cylindrical transmitting head 15
    c. The first jaw 10
    d. The mitral valve: the valve is traversed (the tip of the flexible fine rod acting as a needle)
    e. The second jaw 9
    f. The cylindrical receiving head 14
    g. The hollow tube associated with the cylindrical receiving head 12
6. The rod is then pulled to position the synthetic chordae and remove the rod-needle.

As such, the present invention also relates to a method for fitting a mitral chordal prosthesis using a device 1 according to the invention characterized in that said method comprises steps consisting of:

a. inserting the clamp 11 into the patient's heart with the hollow tubes 12, 13 in the low position,
2. opening the jaws 9,10 in order to grip the mitral valve,
3. locking the clamp 11 in the closed position on the mitral valve.
4. pushing on the hollow tubes 12, 13 to set the tubes in the high position.
5. inserting a flexible thin rod to which a chordal prosthesis is attached in the elements in the following order:
    a. The hollow tube 13 associated with the cylindrical transmitting head 15
    b. The cylindrical transmitting head 15
    c. The first jaw 10
    d. The mitral valve
    e. The second jaw 9
    f. The cylindrical receiving head 14
    g. The hollow tube associated with the cylindrical receiving head 12

The invention claimed is:

1. Surgical device comprising:
a hollow cylinder, a clamp with two jaws, the two jaws comprising an outer surface and an inner surface, pivotably mounted relative to an axis perpendicular to the longitudinal axis of said hollow cylinder between an open position and a closed position, wherein the clamp is arranged extending from the distal end of said hollow cylinder and two hollow tubes, wherein said jaws each comprise a passage from said outer surface to said inner surface, said passages are arranged facing each other when said clamp is in the closed position and in that each of said hollow tubes is associated respectively with one of the jaws in such a way that said hollow tube opens into said passage and in that the distal end of said hollow tubes is rotatably mounted, about an axis perpendicular to the longitudinal axis of said passage, between a high position wherein the distal end of said hollow tube extends from said passage and a low position wherein the distal end of said hollow tube is arranged perpendicularly to said passage.

2. Surgical device according to claim 1, wherein the outer surface of said jaws comprises, at the outer surface thereof, a groove to receive the distal part of said hollow tube when said tube is in the low position.

3. Surgical device according to claim 1, wherein the rotation of said jaws is actuated by a rod positioned wholly or partially in said hollow cylinder, wherein the proximal end opens at the proximal end of said hollow cylinder and wherein the distal end is associated with the proximal end of said jaws.

4. Surgical device according to claim 1, wherein the inner surface of said jaws comprises ribs.

5. Surgical device according to claim 4, wherein said ribs have a triangular transverse profile.

6. Surgical device according to claim 1, wherein said hollow cylinder comprises at the distal end thereof openings arranged extending from said grooves to enable the passage of said hollow tube from inside to outside said hollow cylinder.

7. Surgical device according to claim 1, wherein said hollow cylinder comprises, in the proximal part thereof, openings to enable the passage of said hollow tubes from inside to outside said hollow cylinder.

8. Surgical device according to claim 1, wherein said clamp is associated with said hollow cylinder via an intermediate part comprising a proximal part, the proximal part inserted into the distal end of said hollow cylinder, and a distal part comprising recesses for receiving the axis guiding said jaws in rotation.

9. Surgical device according to claim 1, wherein when said hollow tubes are in the low position and said clamp is closed, the whole device is configured to fit completely into a cylinder having a diameter equal to that of said hollow cylinder.

10. Method for fitting a mitral chordal prosthesis using a device according to claim 1, comprising:
inserting the clamp into the patient's heart with the hollow tubes in the low position,
opening the jaws in order to grip the mitral valve;
locking the clamp in the closed position on the mitral valve;
pushing on the hollow tubes to set the tubes in the high position;
inserting a flexible thin rod to which a chordal prosthesis is attached in elements in the following order:
    the hollow tube associated with the cylindrical transmitting head;
    the cylindrical transmitting head;
    the first jaw;
    the mitral valve;
    the second jaw;
    the cylindrical receiving head; and
    the hollow tube associated with the cylindrical receiving head.

* * * * *